United States Patent [19]

Mourier

[11] 3,971,831

[45] July 27, 1976

[54] PROCESS FOR THE SEMIHYDROGENATION OF CITRAL TO CITRONELLAL

[75] Inventor: Emile Mourier, Sainte-Foy-Les-Lyon, France

[73] Assignee: Rhone-Poulenc S.A., Paris, France

[22] Filed: May 2, 1973

[21] Appl. No.: 356,677

[30] Foreign Application Priority Data

May 4, 1972 France .............................. 72.15883

[52] U.S. Cl. ............................................. 260/601 R
[51] Int. Cl.² ........................................ C07C 47/20
[58] Field of Search ................................ 260/601 R

[56] References Cited
FOREIGN PATENTS OR APPLICATIONS
1,086,447  10/1967  United Kingdom ............. 260/601 R

OTHER PUBLICATIONS

Skita, "Ber. der deut. Chem. Gesell," vol. 42, pp. 1627–1635 (1909).

*Primary Examiner*—Nicholas S. Rizzo
*Assistant Examiner*—David B. Springer

[57] ABSTRACT

A process is provided for the semihydrogenation of the olefinic group in conjugated position to a carbonyl group in citral and homologous dienic aldehydes. The dienic aldehyde is hydrogenated catalytically using a palladium catalyst, and in solution in a lower aliphatic alcohol in the presence of an alkali or alkaline earth metal borate. The process is of particular application to the semihydrogenation of citral to citronellal.

15 Claims, No Drawings

PROCESS FOR THE SEMIHYDROGENATION OF CITRAL TO CITRONELLAL

Citronellal, 3,7-dimethyl-6-octen-al, is found in dextro- and laevo-forms in various essential oils, particularly citronella oil, but it is also found in other volatile oils such as lemon, lemon grass, and melissa oil, and these have been the prime source of supply for this material. Since the supply of such oils is variable, as well as the quality, it would be desirable to develop other sources of supply for this material.

Citronellal has been prepared by oxidation of citronellol with potassium dichromate and sulfuric acid, Tiemann and Schmidt, Berichte 30, 34 (1897). However, the yields were rather poor, because of the formation of many by-products.

Skita, Berichte 42, 1633 (1909), obtained citronellal admixed with other products by hydrogenating citral in alcohol with a palladium catalyst, but the yields were rather poor, and the reaction mixture was difficult to work up.

Citronellal is also prepared commercially from pinene, according to the process described by Webb, U.S. Pat. No. 2,902,495, dated Sept. 1, 1959. 7,8-Epoxy-2,6-dimethyloctane-2-ol is prepared from 2,6-dimethyl-2,7-octadiene, which is obtained by fractionation of the vapor phase pyrolysis product of 1-pinane. The epoxy alcohol is then pyrolyzed with HCl in an iron tube at 400°C. α-Citronellal is obtained in a 58–62% yield, with 20–25% hydrocarbons, water and high boiling compounds. The low yield makes attractive the development of an alternative route.

Citral,3,7-dimethyl-2-6-octadiene-al, is a constituent of oil of lemon grass, and it is also present, to a limited extent, in oils of verbena, lemon, and orange. Until recently, this supply has also been dependent upon the availability of these oils. However, in recent years, syntheses have been developed which make it possible to prepare citral synthetically in a high purity. Among the various methods for preparation of citronellal, the one by hydrogenation of citral is the most advantageous because citral is an easily available commercial material, in addition to the fact that the hydrogenation is performed in generally mild conditions and the realization does not present any really important technical problems.

Citral has two ethylenic groups in nonconjugated positions, and a carbonyl group in conjugated position to the 2-ethylenic group. The critical point of this hydrogenation thus is the selectivity of the catalyst because the ethylenic group not conjugated to the carbonyl group hydrogenates under similar conditions to the conjugated ethylenic group; the carbonyl group can also be hydrogenated. As a result, the semihydrogenation of citral to 3,7-di-methyl-6-octen-al in good yield has proved difficult, and no method is at present available which is capable of producing sufficiently pure citronellal in good yield and sufficiently economically to warrant its use commercially.

Various metal catalysts have been suggested, with proposals to increase their selectivity by addition of activators or by precisely adjusting the operating conditions. Palladium metal has been recognized for a long time (French Pat. No. 474,809) as generally useful for selective hydrogenation of polyethylenic carbonyl compounds comprising ethylenic groups alpha,beta to the carbonyl group. This hydrogenation is performed at ordinary pressure and temperature, and is favored by the use of diluents such as methanol or ethanol. However, the process must be carried out in a completely neutral medium, in order to avoid the side reactions which can take place under the influence of alkali or acid agents.

Due to this structure, the semihydrogenation of citral differs from the hydrogenation of conjugated aromatic aldehydes such as cinnamic aldehydes in which the ethylenic double bond in the side chain is conjugated with the carbonyl group and also with the aromatic conjugated of the benzene ring. Levy and Friedman, U.S. Pat. No. 3,280,192, patented Oct. 18, 1966, discuss the problems that arise in this connection. They point out that the selective reduction of an olefinic linkage in the presence of a readily reducible group such as an aldehyde function usually cannot be achieved directly, and the catalytic hydrogenation of cinnamic aldehyde results in a variety of products and mixtures of products, of which the dihydrocinnamic aldehydes are only one component, including as well cinnamic alcohol, dihydrocinnamic alcohol and dihydrocinnamic aldehyde. Levy and Friedman found that a highly selective hydrogenation of the double bond of cinnamic aldehyde and its lower alkyl substituted derivatives could be effected by employing palladium and an aqueous alkaline reaction medium for the hydrogenation. When such a combination is used, the hydrogenation proceeds with substantially no formation of the undesirable alcohol by-product, and the process finds an automatic end point in that the absorption of hydrogen ceases when only the olefinic double bond is saturated. However, Levy and Friedman do not indicate that the process is applicable to conjugated olefinic aldehydes containing a second nonconjugated ethylenic group, but confine their description to aromatic aldehydes of the type of cinnamic aldehyde. They also point out that when a one-phase alcohol solution is used in their process, mixtures of the possible reaction products or, in some cases, the olefinic alcohol, are obtained, and consequently they require that the aqueous alkaline medium be present in a separate phase from the cinnamic aldehyde, and an alcohol is not present. The data in Table I shows, for instance, that the reduction with platinum oxide of p-tertiary-butyl-alpha-methylcinnamic aldehyde in ethanol containing 0.2% sodium hydroxide gives a negligible yield of dihydrocinnamic aldehyde, and mostly cinnamic alcohol, confirming the necessity of avoiding a one-phase alcohol solution for the reaction.

Levy and Friedman in British Pat. No. 1,086,447, published Oct. 11, 1967, extend the disclosure of U.S. Pat. No. 3,280,192, somewhat, and indicate that citronellal can be hydrogenated to dimethyl octanal at from 50° to 80°C., using aqueous sodium carbonate solution and palladium on charcoal, in a 93.5% yield. This suggests that selective hydrogenation of the olefinic group conjugated with the aldehyde group is rather difficult to achieve, using a palladium catalyst, in the presence of which they had indicated in U.S. Pat. No. 3,280,192 that cinnamic aldehyde is converted to an alcohol (see Table I).

It has been reported (J. Applied Chem. USSR 10, 119-25) that hydrogenation of citral can result in a 64% yield of citronellal, but such a yield is certainly unsatisfactory for use commercially.

Givaudan German Offenlegungsschrift No. 2,114,211, published Oct. 14, 1971, Belgian Pat. No.

764,840, describe the hydrogenation of citral in good yield, with very little unconverted citral, very little dimethyl octanal, and practically no citronellol, isopulegol or dimethyl octanol, by using a palladium catalyst in the presence of a small amount of water and a base. No organic solvent is used. Strong, moderately strong, and weak bases can be used, as well as organic amines. In the Examples, no yield data are given, merely the analysis of the composition of the product by vapor phase chromatography, which gives no indication of the amount of polymer or other nonvolatile residue formed. However, although under these conditions, the hydrogenation takes place more selectively, reaction times of several hours are needed or else one must work under pressure, in order to achieve a faster reaction. The yield of citronellal is only of the order of 78% since relatively large amounts of polymerization products and tars are formed, because of the presence of alkali during the hydrogenation of citral, and also during the distillation of crude citronellal.

It was, therefore, necessary to find a process which would permit selective hydrogenation of citral to citronellal at a faster rate, allowing the separation of the citronellal by the distillation, and avoiding the formation of by-products and tars.

In accordance with the instant invention, a process is provided for the selective hydrogenation of the olefinic group in a conjugated position to the carbonyl group in citral and homologous dienic aldehydes, in the presence of a palladium catalyst and hydrogen gas in alcoholic reaction medium in the presence of a specific and carefully selected alkaline agent, an alkali metal or alkaline earth metal salt of an oxyacid of boron, with separation of the citronellal or homologous unsaturated aldehydes by distillation of the solvent.

The reaction proceeds at room temperature and at atmospheric pressure, although higher temperatures and higher pressures can be used, if desired. The dienic aldehyde is present in the same phase as the alcohol and the alkaline agent. Preferably, no water is present, but a small amount, not in excess of that soluble in the reaction medium, and less than 0.1%, can be present, if desired, or if the reactants are not anhydrous.

The process of the invention is applicable to citral and to homologous dienic aldehydes having the formula:

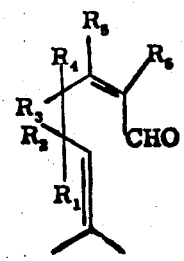

wherein $R_1$, $R_2$, $R_3$, $R_4$, and $R_6$ are selected from the group consisting of hydrogen and lower alkyl groups having from one to about five carbon atoms and $R_5$ is a lower alkyl group having from one to about five carbon atoms. The R alkyl groups can be straight chain or branched chain.

Exemplary R alkyl groups include methyl, ethyl, propyl, isopropyl, butyl, sec-butyl, tert-butyl, isobutyl, amyl, isoamyl, and tert-amyl.

The process of the invention is of particular application to citral 3,7-dimethyl-2,6-octadiene-al which can be converted to citronellal in yields in excess of 95%. In the case of citral, the reaction proceeds as follows:

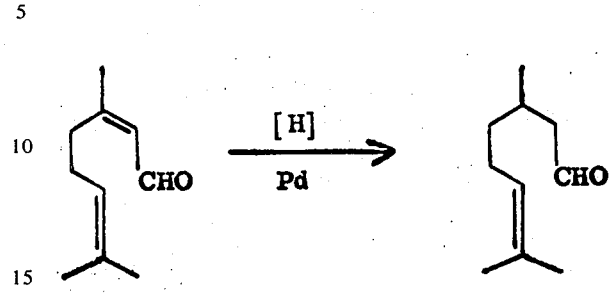

The process is applicable to both geometric isomers of citral, geranial and neral, as well as to the lower alkyl homologues of citral.

Other aldehydes to which the invention is applicable include:
3-ethyl-7-methyl-2,6-octadiene-al
3-isobutyl-7-methyl-2,6-octadiene-al
3-amyl-7-methyl-2,6-octadiene-al
2,3,4,5,7-pentamethyl-2,6-octadiene-al
3,5,7-trimethyl-2,6-octadiene-al
3,4,4,5,5,7-hexamethyl-2,6-octadiene-al
2,4,7-trimethyl-3-isopropyl-2,6-octadiene-al
2,3,7-trimethyl-2,6-octadiene-al
3,4,7-trimethyl-2,6-octadiene-al
3,4,4,7-tetramethyl-2,6-octadiene-al
3-isopropyl-7-methyl-2,6-octadiene-al
3-propyl-7-methyl-2,6-octadiene-al
3,7-dimethyl-4-ethyl-2,6-octadiene-al
3-butyl-7-methyl-2,6-octadiene-al
3-isobutyl-7-methyl-2,6-octadiene-al
3,7-dimethyl-4-isopropyl-2,6-octadiene-al It is essential that the hydrogenation be carried out in the presence of a lower aliphatic alcohol having from one to about five carbon atoms, such as methanol, ethanol, propanol, isopropanol, butanol, 2-butanol, tert-butanol, isobutanol, pentanol, isopentanol, sec-pentanol and tert-pentanol.

Usually, an amount of alcohol at least about 10% by weight of the dienic aldehyde increases reaction rate satisfactorily. There is no upper limit on the amount and since the alcohol can serve as a solvent, it can be present in a considerable excess. However, unduly dilute solutions increase handling difficulties, because of the greater volumes of material, and are not normally practical. Consequently, the amount of alcohol is usually not in excess of about 200% and preferably is not in excess of about 150% by weight of the dienic aldehyde.

The borate can be any alkali metal or alkaline earth metal salt of an oxyacid of boron, such as metaboric acid, orthoboric acid or pyroboric acid. Among these salts, sodium, calcium and potassium borates are readily available commercially, and offer the advantage of being soluble in lower aliphatic alcohols.

As the hydrogenation catalyst, palladium in any form can be used, but preferably the palladium is supported on a suitable inert carrier such as charcoal, alumina, barium sulfate, calcium carbonate, aluminum sulfate, carbon, silicates, clays, aluminates, and silica gel. The palladium metal is preferably in finely divided form. The palladium metal can be obtained by reduction of palladium salts such as chlorides, nitrates or palladium oxides, with various reducing agents. Palladium metal can also be precipitated on any inert support.

The amount of palladium required is quite small; as little as 0.001 g of palladium metal per 100 g of the dienic aldehyde is satisfactory. Amounts of up to about 1 g of palladium metal per 100 g can be used, but amounts larger than this, although satisfactory, are uneconomic, and would not therefore be employed. Preferably, the amount is within the range from about 0.005 g to about 0.1 g per 100 g of dienic aldehyde.

The addition of alkali metal or alkaline earth metal borate increases the yield. The addition of borate should be in an amount of at least about 0.05% by weight of the dienic aldehyde. Larger amounts of borate can be used, but normally the amount of borate is not in excess of about 5%, and preferably from about 0.1 to about 3%. The excess of solvent can be recovered by distillation and recycled in the next operation.

The starting materials, i.e., the dienic aldehyde, alcohol, borate, and catalyst, are mixed in a hydrogenation apparatus, and hydrogen then introduced until a hydrogen atmosphere is obtained, at atmospheric pressure or at elevated pressure, preferably ranging from about 5 psi to about 30 psi. Pressures up to 500 psi can be used, if desired. The reaction mixture is then agitated under hydrogen until the desired amount of hydrogen is taken up, at which time the hydrogenation of the olefinic group in a conjugated position to the carbonyl group has been substantially completed. The catalyst can then be removed and the semihydrogenated reaction product used as is or purified by distillation.

The reaction can be carried out at temperatures as low as about 10°C. It is usually convenient to conduct the reaction at a temperature at or below the boiling point of the alcohol used, which is 65°C. in the case of methanol, and 138°C. in the case of pentanol-1; preferably the temperature is not more than 40°C. By use of hydrogen pressures above atmospheric, temperatures up to 10°C. above the boiling point can be used. Generally, a temperature within the range from about 10° to about 60°C. is useful. There however is no upper limit on reaction temperature, except that imposed by the stability of the dienic aldehyde and/or the olefinic aldehyde reaction product.

The reaction proceeds rather rapidly, depending upon temperature, hydrogen concentration, amount of alcohol, and catalyst concentration. Usually, the reaction does not require more than 20 hours for completion, and may be complete in as little as one-half hour.

The separation of the solvent is done by distillation in the presence of a certain amount of water which is sufficient so that the boric acid salt is maintained in solution during this separation. Under these conditions, and this is another aspect of the invention, it has been found surprisingly that the boron compound stabilizes the citronellal or homologue thereof which has been formed, and the latter is no longer subject to degradation when it is heated during the process of removal of the solvent. This stabilizing action, which is exerted by the salts of the oxyacids of boron is shown in the Examples, is obtained when solvent is recovered by distillation from any reaction medium containing citronellal and its homologues, prepared by any semihydrogenation process using hydrogen and a palladium catalyst.

When the distillation is finished, the citronellal or homologue thereof is separated from the aqueous layer by simple decantation, and is in a sufficient purity to be suitable for direct use in certain reactions, as for instance, preparation of hydroxy citronellal. It can also be subjected to a purification treatment, if it is to be used in perfumery.

Another advantage of the process is that activity of the catalyst is preserved so that it can be used in several successive operations without the necessity of purification or regeneration prior to recycling. The long life of the catalyst, the short length of the hydrogenation reaction and a moderate temperature and pressure, and the possibility to recover the solvent by distillation without decomposition of citronellal, are the important factors which permit obtaining the product in good yields and high degree of purity.

The following Examples in the opinion of the inventors represent preferred embodiments of the invention:

EXAMPLE 1

The reaction was carried out in a 1 liter container provided with sufficient agitation (agitator rotated at 700 rotations per minute), jacketed for external cooling with cold water, provided with a dropping funnel for addition of liquid, and connected to a source of hydrogen which volume can be measured.

The atmosphere in the reactor was replaced with nitrogen, 8 g of 5% palladium on carbon black was added, as well as 0.4 g of sodium borate technical grade (borax) and 240 g of methanol. In the dropping funnel connected to the reactor were placed (under nitrogen) 163.5 g of technical grade citral, analyzing 93% citral, (i.e. 1 mole) 1.5% high boilers and 5.5% low boiling impurities. The nitrogen atmosphere was replaced by hydrogen. The citral was added into the reactor which was kept at 20°C., where the hydrogen pressure was adjusted to 80 g/cm$^2$. The hydrogenation reaction was discontinued within about 1 hour, when 105% of theory hydrogen had been absorbed. After substituting the hydrogen atmosphere with nitrogen, the reaction mixture was filtered for separation of the catalyst. By gas vapor chromatographic analysis of an aliquot, it was found that the yield of the semihydrogenation was: 92.8% citronellal, 5.6% dihydrocitronellal, and 1.6% high boilers based on citral reacted. The citral had reacted to the extent of 99.7%. After addition of 14 g water to the filtrate, the mixture was submitted to distillation at atmospheric pressure through a 300 mm column filled with Multiknit rings at a pot temperature of 99°–100°C. This distillation was stopped when the vapor temperature on top of the column reached 90°C. (after 6 hours, which was calculated to correspond to the conditions of a typical plant distillation). The reaction mass was cooled to about 25°C., and the aqueous layer separated by decantation.

There were thus obtained 166 g crude (analyzing 83.5% citronellal, 5% dihydrocitronellal, 5% high boilers, 5.76% low-boiling impurities, 0.6% water and 0.14% hydroxyisopulegol). The true yield of citronellal was 90%, dihydrocitronellal 5.3% and low and high boilers, and isopulegol, 0.4%, 3.8%, and 0.15%, respectively. The catalyst from the above described reaction was used in ten successive hydrogenations, without any noticeable decline in activity; for instance, the duration of the hydrogenations never exceeded 1 hour.

EXAMPLES 2 TO 5

Further examples were run similarly to Example 1 but without borax (Example 2), with borax but in a strictly anhydrous medium (Example 3), and replacing borax with NaOH (Example 4) or with Ba(OH)₂ (Example 5).

The results are presented in Table I, one set of results for the hydrogenation step and another one after distillation of the solvent at atmospheric pressure in presence of water.

about 5% by weight of the dienic aldehyde, the alkanol being in an amount within the range from about 10% to about 200% by weight of the dienic aldehyde, in the presence of at most 0.1% water.

2. The process of claim 1, in which the aldehyde is citral, 3,7-dimethyl-2,6-octadiene-al, which is con-

TABLE I

| | | RESULTS AFTER HYDROGENATION | | | | | RESULTS AFTER DISTILLATION | | | | |
|---|---|---|---|---|---|---|---|---|---|---|---|
| Example | Base g | %² Low Boilers | %² High Boilers | % Yield Citronellal | % Yield Dihydro Citronellal | % Citral Reacted | %² Low Boilers | %² High Boilers | %² Isopulegol | % Yield Citronellal | % Yield Dihydro Citronellal |
| 1 | Borax 0.4 | 0 | 1.6 | 92.8 | 5.6 | 99.7 | 0.4 | 3.8 | 0.15 | 90 | 5.3 |
| 2 | None | 0.8 | 3 | 84 | 9 | 99.7 | 5.8 | 5.1 | 0.6 | 76.3 | 8.8 |
| 3¹ | Borax 0.4 | 0.2 | 0.5 | 92.8 | 6.6 | 99.7 | 0.6 | 2.7 | 0.15 | 90 | 6.3 |
| 4 | NaOH 4×10⁻⁴ | 0 | 10 | 84.4 | 5.5 | 99.8 | 0.3 | 15.8 | 4.9 | 73.5 | 5.3 |
| 5 | Ba(OH)₂ 0.5 g | 0.2 | 15 | 63.3 | 5 | 85 | 2.5 | 20.8 | 5.4 | 57.8 | 4.9 |

¹For the example in strictly anhydrous medium, the borax as well as the palladium/carbon catalyst were dried in an oven until constant weight, while the methanol was distilled under sodium.
²By weight.

It appears from these Examples that the presence of borax is beneficial in both steps of the process: the hydrogenation, and the distillation of the solvent in the presence of water at atmospheric pressure.

It is also clear that carrying the hydrogenation in the absence of water does not diminish the yield, since the slight decline in selectivity (% of dihydrocitronellal present) is compensated for by the reduced amount of high boiling products. It can also be concluded that the borax affords a better selectivity.

Having regard to the foregoing disclosure, the following is claimed as the inventive and patentable embodiments thereof:

1. In the process for the selective hydrogenation of the olefinic group in a conjugated position to the carbonyl group in dienic aldehydes having the formula:

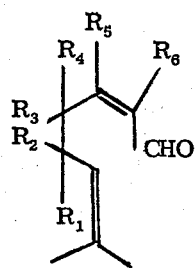

wherein $R_1, R_2, R_3, R_4$ and $R_6$ are selected from the group consisting of hydrogen and lower alkyl groups having from one to about five carbon atoms and $R_5$ is a lower alkyl group having from one to about five carbon atoms, which comprises hydrogenating the dienic aldehyde in the presence of a palladium metal catalyst, alkali and water, the improvement which comprises carrying out the hydrogenation at a temperature above about 10°C and at a pressure within the range from atmospheric pressure to about 500 psi in the presence of a palladium metal catalyst in an amount within the range from about 0.001 g to about 1 g of palladium metal per 100 g of dienic aldehyde in solution in a lower alkanol having from one to about five carbon atoms with an alkali or alkaline earth metal salt of a boric acid in an amount of at least about 0.05% up to verted to citronellal.

3. The process of claim 1, in which the aldehyde is selected from the group consisting of:
   3-ethyl-7-methyl-2,6-octadiene-al
   3-isobutyl-7-methyl-2,6-octadiene-al
   3-amyl-7-methyl-2,6-octadiene-al
   2,3,4,5,7-pentamethyl-2,6-octadiene-al
   3,5,7-trimethyl-2,6-octadiene-al
   3,4,4,5,5,7-hexamethyl-2,6-octadiene-al
   2,4,7-trimethyl-3-isopropyl-2,6-octadiene-al
   2,3,7-trimethyl-2,6-octadiene-al
   3,4,7-trimethyl-2,6-octadiene-al
   3,4,4,7-tetramethyl-2,6-octadiene-al
   3-isopropyl-7-methyl-2,6-octadiene-al
   3-propyl-7-methyl-2,6-octadiene-al
   3,7-dimethyl-4-ethyl-2,6-octadiene-al
   3-butyl-7-methyl-2,6-octadiene-al
   3-isobutyl-7-methyl-2,6-octadiene-al
   3,7-dimethyl-4-isopropyl-2,6-octadiene-al.

4. The process of claim 1, in which the salt of the boric acid is an alkali metal salt of boric acid.

5. The process of claim 1, in which the alkanol is selected from the group consisting of methanol and ethanol.

6. The process of claim 1, in which the amount of alcohol is at least about 10% up to about 200% by weight of the dienic aldehyde.

7. The process of claim 1, in which the amount of boric acid salt is at least about 0.05% up to about 5% by weight of the dienic aldehyde.

8. The process of claim 1, in which the hydrogenation is conducted at atmospheric pressure at a temperature from about 10°C. to about 60°C.

9. The process of claim 1, in which the hydrogen is at a pressure within the range from atmospheric pressure up to about 500 psi.

10. The process of claim 1, in which the reaction medium comprises water in an amount up to about 0.1% by weight of the alcohol.

11. The process of claim 1, in which the palladium metal is supported on an inert carrier.

12. The process of claim 1, in which the amount of palladium metal is within the range from about 0.001 g to about 1 g palladium metal per 100 g of dienic aldehyde.

13. The process of claim 1, in which the catalyst is palladium metal on carbon black, and the boric acid salt is sodium or potassium borate.

14. The process of claim 1, in which the reaction mixture is agitated under hydrogen until the desired amount of hydrogen is absorbed, and the hydrogenation of the olefinic group in a conjugated position to the carbonyl group has been substantially completed, the catalyst is removed, and the reaction product recovered by distillation of the lower alkanol in the presence of the boric acid salt.

15. The process of claim 1, in which the reaction is carried out at a temperature within the range from about 10° to about 40°C.

* * * * *